(12) United States Patent
Hu et al.

(10) Patent No.: US 7,033,818 B2
(45) Date of Patent: Apr. 25, 2006

(54) RECOMBINANT POLYKETIDE SYNTHASE GENES

(75) Inventors: Zhihao Hu, Hayward, CA (US); Robert McDaniel, Palo Alto, CA (US); Daniel V. Santi, San Francisco, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 227 days.

(21) Appl. No.: 10/125,815

(22) Filed: Apr. 18, 2002

(65) Prior Publication Data

US 2002/0173008 A1 Nov. 21, 2002

Related U.S. Application Data

(63) Continuation-in-part of application No. 09/679,279, filed on Oct. 4, 2000, now Pat. No. 6,524,841.

(60) Provisional application No. 60/190,024, filed on Mar. 17, 2000, provisional application No. 60/158,305, filed on Oct. 8, 1999.

(51) Int. Cl.
*C12N 1/20* (2006.01)
*C07H 21/04* (2006.01)

(52) U.S. Cl. .............. 435/252.33; 435/254.2; 435/320.1; 435/471; 536/23.2; 536/23.1

(58) Field of Classification Search .............. 536/23.2, 536/23.7; 435/320.1, 252.3, 252.35
See application file for complete search history.

(56) References Cited

U.S. PATENT DOCUMENTS

| | | | |
|---|---|---|---|
| 3,819,611 A | 6/1974 | Weinstein et al. | 260/210 |
| 5,672,491 A | 9/1997 | Khosla et al. | 435/148 |
| 5,824,513 A | 10/1998 | Katz et al. | 435/76 |
| 5,962,290 A | 10/1999 | Khosla et al. | 435/183 |
| 6,066,721 A | 5/2000 | Khosla et al. | 536/23.1 |
| 6,080,555 A | 6/2000 | Khosla et al. | 435/41 |
| 6,117,659 A | 9/2000 | Ashley et al. | 435/155 |
| 6,251,636 B1 | 6/2001 | Betlach et al. | 435/76 |
| 6,265,202 B1 | 7/2001 | Sherman et al. | 435/252.31 |

FOREIGN PATENT DOCUMENTS

| | | |
|---|---|---|
| WO | WO 97/23630 | 7/1997 |
| WO | WO 98/49315 | 11/1998 |
| WO | WO 99/05283 | 2/1999 |
| WO | WO 99/61599 | 12/1999 |
| WO | WO 00/00500 | 1/2000 |
| WO | WO 00/24907 | 5/2000 |
| WO | WO 00/63361 | 10/2000 |
| WO | WO 01/27284 | 4/2001 |

OTHER PUBLICATIONS

Bedford et al. A functional chimeric modular polyketide synthase generated via domain replacement. Chemistry & Biology (1996) 3: 827-831.*

(Continued)

*Primary Examiner*—Nashaat T. Nashed
(74) *Attorney, Agent, or Firm*—Morrison & Foerster LLP

(57) ABSTRACT

Regions of sequence identity are recurrent in some modular polyketide synthase (PKS) gene clusters. Such sequences are potentially detrimental to the stability of PKS gene clusters and expression plasmids for the genes in the gene cluster. PKS gene and gene cluster stability can be improved, and reproducible polyketide titers can be obtained using those genes and gene clusters when the regions of sequence identity are reduced or eliminated by replacing one or more identical or homologous segments with non-homologous segments that encode the same or a substantially similar amino acid sequence.

13 Claims, 4 Drawing Sheets

OTHER PUBLICATIONS

Carreras et al, Current Opinion in Biotechnology (1998) 9(4):403-411.
Hutchinson, Current Opinion in Microbiology (1998) 1(3): 319-329.
Kao et al., Science (1994) 265:509-512.
Katz, Chemical Reviews (1997) 97(7):2557-2575.
Liu et al., Annual Review of Microbiology (1994) 48:223-256.
Malpartida et al., Nature (1987) 325:818-821.
McDaniel et al., Proceedings of the National Academy of Sciences of USA (1999) 96:1846-1851.
Nakagawa et al., Macrolide Antibiotics, Omura (ed.) Publisher: Academic, Orlando, Florida (1984) pp. 37-84.
Olano et al., Molecular and General Genetics (1998) 259 (3):299-308.
Otten et al., Journal of Bacteriology (1995) 177(22):6688-6692.
Otten et al., Journal of Bacteriology (1997) 179(13):4446-4450.
Summers et al., Microbiology (1997) 143:3251-3262.
Swan et al., Molecular and General Genetics (1994) 242(3): 358-362.
Torkkell et al., Molecular and General Genetics (1997) 256(2):203-209.
Volchegursky et al., Molecular Microbiology (2000) 37(4): 752-762.
Xue et al., Proc. Natl. Acad. Sci. USA (1998) 95:12111-12116.
Cortes et al., Letters to Nature (1990) 348:176-178.
Desai et al., Journal of Microbiology & Biotechnology (2002) 28: 297-301.
Weber et al., Journal of Bacteriology (1990) 172:2372-2383.

* cited by examiner

Figure 1
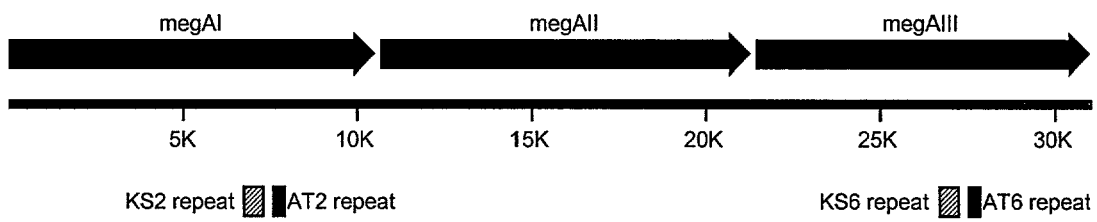
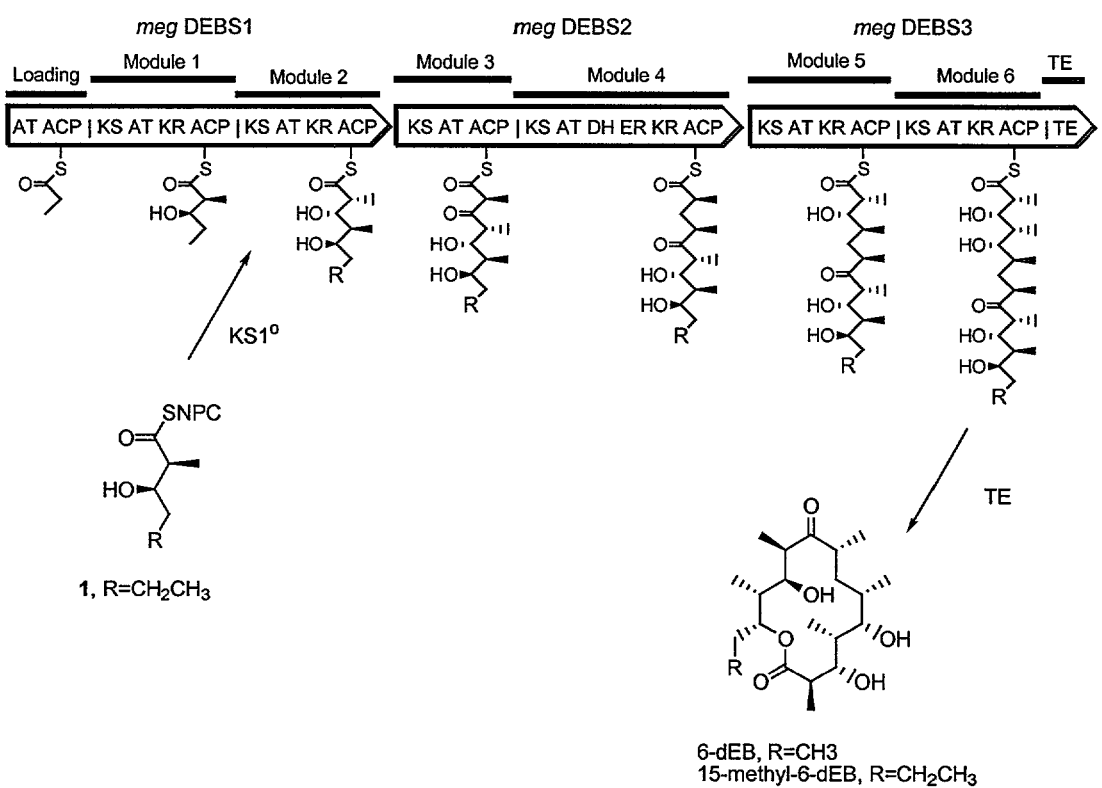
6-dEB, R=CH3
15-methyl-6-dEB, R=CH2CH3

Figure 2

```
             Pst I
megKS2/6   1 TGCAGCGGTTGTCGGTGGCGGTGCGGGAGGGGCGTCGGGTGTTGGGTGTGGTGGTGGGTTCGGCGGTGAATCAGGATGGG
megKS6*    1 TGCAGCGCCTCTCCGTCGCCGTCCGCGAGGGCCGCCGAGTCCTCGGCGTCGTCGTCGGCTCGGCCGTCAACCAAGACGGC
             *******  *       *        *       * megKS2/6  81 GCGAGTAATGGGTTGGCGGCGCCGTCGGGGGTGGCGCAGCAGCGGGTGATTCGGCGGGCGTGGGGTCGTGCGGGTGTGTC
megKS6*   81 GCGTCAAACGGCCTCGCCGCGCCCTCCGGCGTCGCCCAGCAGCGCGTCATACGCCGCGCGTGGGGACGCGCCGGAGTATC
             ***    **  **    *  ** ***** **  ** ** ** ** ********  **  ** **  ******** **  ** ** ** **

BamH I
megKS2/6 161 GGGTGGGGATGTGGGTGTGGTGGAGGCGCATGGGACGGGGACGCGGTTGGGGGATCCGGTGGAGTTGGGGGCGTTGTTGG
megKS6*  161 GGGCGGCGACGTCGGAGTCGTCGAGGCCCACGGCACCGGCACCCGCCTCGGGGATCCCGTCGAGCTGGGCGCCCTCCTGG
             *         *        *  ******   *    *  *** megKS2/6 241 GGACGTATGGGGTGGGTCGGGGTGGGGTGGGTCCGGTGGTGGTGGGTTCGGTGAAGGCGAATGTGGGTCATGTGCAGGCG
megKS6*  241 GCACGTACGGCGTCGGCCGCGCGGCGTCGGCCCGGTCGTCGTCGGCAGCGTCAAGGCCAACGTCGGCCACGTCCAGGCC
              * ***         * **           *     *** megKS2/6 321 GCGGCGGGTGTGGTGGGTGTGATCAAGGTGGTGTTGGGGTTGGGTCGGGGGTTGGTGGGGTCCGATGGTGTGTCGGGGTGG
megKS6*  321 GCGGCCGGCGTCGTCGGGGTCATCAAGGTCGTCCTCGGCCTCGGCCGCGGGCTGGTCGGCCCGATGGTCTGCCGCGGCGG
             ***        ******      * **   *   *     ******      ** megKS2/6 401 GTTGTCGGGGTTGGTGGATTGGTCGTCGGGTGGGTTGGTGGTGGCGGATGGGGTGCGGGGGTGGCCGGTGGGTGTGGATG
megKS6*  401 CCTCAGCGGCCTCGTCGACTGGTCGTCCGGCGGCCTCGTCGTCGCGGACGGGGTCCGCGGCTGGCCGGTCGGCGTCGACG
              *    ** **  *  ** ** ********  ** **    **** ** *****  ** **   *********  ** **  *

Bsm I
megKS2/6 481 GGGTGCGTCGGGGTGGGGTGTCGGCGTTTGGGGTGTCGGGGACGAATGCTCATGTGGTGGTGGCGGAGGCGCCGGGGTCG
megKS6*  481 GCGTCCGCCGGGGCGGCGTCTCGGCGTTCGGCGTCAGCGGGACGAATGCTCATGTGGTGGTGGCGGAGGCGCCGGGGTCG
             *    ***    ****     ****************************************** megKS2/6 561 GTGGTGGGGGCGGAACGGCCGGTGGAGGGGTCGTCGCGGGGGTTGGTGGGGGTGG 615
megKS6*  561 GTGGTGGGGGCGGAACGGCCGGTGGAGGGGTCGTCGCGGGGGTTGGTGGGGGTGG 615
             *******************************************************
```

---

```
megAT2/6   1 CCGGTGTGGTGTCGGGGGTGGCGTCGGGTGGTGGTGTGGTGTTTGTTTTTCCTGGTCAGGGTGGTCAGTGGGTGGGGATG
megAT6*    1 CCGGTGTGGTGTCGGGGGTGGCGTCGGGTGGTGGTGTGGTGTTTGTTTTTCCTGGTCAGGGTGGTCAGTGGGTGGGGATG
             *******************************************************************************

SfaN I
megAT2/6  81 GCGCGGGGGTTGTTGTCGGTTCCGGTGTTTGTGGAGTCGGTGGTGGAGTGTGATGCGGTGGTGTCGTCGGTGGTGGGGTT
megAT6*   81 GCGCGGGGGTTGTTGTCGGTTCCGGTGTTTGTGGAGTCGGTCGTGGAGTGCGATGCGGTCGTGTCGAGCGTCGTCGGCTT
             ***************************************  *****  **** ***          ** megAT2/6 161 TTCGGTGTTGGGGGTGTTGGAGGGTCGGTCGGGTGCGCCGTCGTTGGATCGGGTGGATGTGGTGCAGCCGGTGTTGTTCG
megAT6*  161 CAGCGTGCTGGGCGTCCTGGAGGGCCGCAGCGGCGCCCCGAGCCTGGACCGCGTCGACGTGGTCCAGCCGGTCCTGTTCG
                  *****     *  *    *     * ****   **** megAT2/6 241 TGGTGATGGTGTCGTTGGCGCGGTTGTGGCGGTGGTGTGGGGTTGTGCCTGCGCGGTGGTGGGTCATTCGCAGGGGGAG
megAT6*  241 TGGTCATGGTCAGCCTGGCCCGCCTGTGGCGCTGGTGCGGCGTGGTCCCGGCCGCCGTGGTCGGCCACAGCCAGGGCGAG
             ** *         ***  ****         ***   ***  * megAT2/6 321 ATCGCGGCGGCGGTGGTGGCGGGGGTGTTGTCGGTGGGTGATGGTGCGCGGGTGGTGGCGTTGCGGGCGCGGGCGTTGCG
megAT6*  321 ATCGCCGCCGCGGTCGTGGCCGGCGTCCTGAGCGTCGGCGACGGCGCCCGCGTCGTGGCCCTGCGCGCCCGCGCCCTGCG
             *****  ** ***** **** **   **  **  ** ** ** ** ***  ** ** ** ** ** **  **** *****  ** ****

Fse I
megAT2/6 401 GGCGTTGGCCGGCCACGGCGGCATGG 426
megAT6*  401 CGCCCTGGCCGGCCACGGCGGCATGG 426
              **  **********************
```

RECOMBINANT POLYKETIDE SYNTHASE GENES

CROSS-REFERENCE TO RELATED APPLICATIONS

This application is a continuation-in-part of U.S. patent application Ser. No. 09/679,279, filed 4 Oct. 2000, now U.S. Pat. No. 6,524,841, which claims priority to now lapsed U.S. provisional patent application Ser. Nos. 60/190,024, filed 17 Mar. 2000, and 60/158,305, filed 8 Oct. 1999, each of which is incorporated herein by reference.

FIELD OF THE INVENTION

The present invention provides methods for increasing production of polyketides and polyketide synthase (PKS) proteins. Polyketides are a diverse class of compounds with a wide variety of activities, including activities useful for medical, veterinary, and agricultural purposes. A number of plasmid-based heterologous expression systems have been developed for the engineering and expression of PKS genes and gene clusters, including multiple-plasmid systems for combinatorial biosynthesis (see U.S. Pat. No. 6,033,883, incorporated herein by reference). The present invention provides methods for improving polyketide production by engineering the genes that encode PKS enzymes. The present invention therefore relates to the fields of molecular biology, chemistry, recombinant DNA technology, medicine, animal health, and agriculture.

BACKGROUND OF THE INVENTION

Modular PKS enzymes are large, multi-subunit enzyme complexes that perform the biosynthesis of polyketide secondary metabolites. See O'Hagan, D., 1991 (a full citation of any reference referred to herein by last name of first author and year of publication is located at the end of this section). Examples of polyketides made by modular PKS enzymes include the antibiotic erythromycin, the immunosuppressant FK506, and the antitumor compound epothilone. See also PCT patent publication No. 93/13663 (erythromycin); U.S. Pat. No. 6,303,342 B1 (epothilone); U.S. Pat. No. 6,251,636 B1 (oleandolide); PCT publication WO 01/27284 A2 (megalomicin); U.S. Pat. No. 5,098,837 (tylosin); U.S. Pat. No. 5,272,474 (avermectin); U.S. Pat. No. 5,744,350 (triol polyketide); and European patent publication No. 791,656 (platenolide), each of which is incorporated herein by reference. A large interest in these enzyme systems lies in the ability to manipulate the specificity or sequence of reactions catalyzed by PKSs to produce novel therapeutic compounds. See McDaniel, R., et al., 2001, and Weissman, K. J et al. 2001. A number of plasmid-based heterologous expression systems have been developed for the engineering and expression of PKSs, including multiple-plasmid systems for combinatorial biosynthesis. See McDaniel, et al., 1993, Xue, et al., 1999, and Ziermann, et al., 2000, and U.S. Pat. Nos. 6,033,883 and 6,177,262; and PCT publication Nos. 00/63361 and 00/24907, each of which is incorporated herein by reference.

In modular PKSs, active sites called "domains" are arranged in groups called "modules" that perform a single round of polyketide chain extension and modification (FIG. 1). PKS modules are typically between ~3.5–7 kb, depending on the number of actives sites present in the module. Frequently the homology between similar active site domains (e.g. ketosynthase (KS), acyltransferase (AT), or ketoreductase (KR)) of a cognate PKS is greater than between domains of heterologous PKSs. Many sequenced PKS gene clusters contain at least two domains in which the DNA sequence identity is greater than 99% over significant lengths of nucleotide bases (i.e. >500 bp). For example, the KR and acylcarrier protein (ACP) domains from modules 2 and 5 of the oleandomycin PKS (see Shah et al., 2000, Swan, D. G., et al., 1994, and U.S. Pat. No. 6,251,636, incorporated herein by reference) each contain a 1,211 bp contiguous segment with 100% identity. In the tylosin PKS (see DeHoff et al., 1996), three 2,013–2,290 bp fragments from the KS and AT domains of modules 1, 4, and 6 all share a sequence identity greater than 99.5%. These repetitive sequences most likely arise from gene duplications or gene conversion during the evolution of the PKS. While these regions appear to be stable in the chromosome of the host organisms in which they are found, such duplications are potentially detrimental to the stable expression of plasmid-borne PKSs in hosts capable of homologous recombination.

The megalomicin 6-deoxyerythronolide B (6-dEB) synthase (meg DEBS, FIG. 1) contains duplicate regions comprising 615 bp in the KS domains and 426 bp in the AT domains of module 2 and module 6. The erythromycin 6-dEB synthase (ery DEBS) is identical in overall genetic architecture to meg DEBS (see Volchegursky, Y., et al., 2000), but does not possess any such redundant sequences. Recently, it was reported that both ery and meg DEBS produced similar yields of 6-dEB in *Streptomyces lividans* (see Volchegursky, Y., et al., 2000). In subsequent rounds of fermentation, titers from meg DEBS were consistently lower than those from ery DEBS. Furthermore a significant decrease in titers was observed when meg DEBS was expressed in *S. coelicolor* CH999, and titers could not be determined reproducibly. This titer decrease and lack of reproducible titer may relate to the regions of homology that are present in the meg but not the ery DEBS. Thus, there exists a need for methods to improve PKS genes that contain such regions of homology. The present invention provides methods and compositions to meet this and other needs.

The following articles provide background information relating to the invention and are incorporated herein by reference.

DeHoff et al. 1996. GenBank accession #U78289.
Desai et al. 2002. J. md. Microbiol. Biotech. 28:297–301.
Jacobsen et al. 1997. Science. 277:367–369.
Kao et al. 1996. Biochem. 35:12363–12368.
Kieser et al. 2000. Practical Streptomyces Genetics. The John Innes Foundation, Norwich, UK.
Leaf et al. 2000. Biotechnol. Prog. 16:553–556.
MacNeil et al. 1992. Gene. 115:119–125.
McDaniel et al. 1993. Science. 262:1546–1557.
McDaniel et al. 2001. In Kirst et al. (ed), Enzyme technologies for pharmaceutical and biotechnological applications, p. 397–426. Marcel Dekker, Inc., N.Y.
O'Hagan, D. 1991. The polyketide metabolites. Ellis Horwood, Chichester, UK.
Sambrook, J., E. F. Fritsch, and T. Maniatis. 1989. Molecular Cloning: A Laboratory Manual, 2nd ed. Cold Spring Harbor Laboratory Press, Plainview, N.Y.
Shah et al. 2000. J. Antibiotics. 53:502–508.
Swan et al. 1994. Mol. Gen. Genet. 242:358–362.
Tang et al. 2000. Chem. & Biol. 7:77–84.
Tsai et al. 1987. Mol. Gen. Genet. 208:211–218.
Volchegursky et al. 2000. Mol. Microbiol. 37:752–762.
Weissman et al. 2001. In H. A. Kirst et al. (ed.), Enzyme technologies for pharmaceutical and biotechnological applications, p. 427–470. Marcel Dekker, Inc., N.Y.

Xue et al. 1999. Proc. Natl. Acad. Sci. U.S.A. 96:11740–11745.

Ziermann et al. 2000. J. Ind. Microbiol. Biotech. 24:46–50.

SUMMARY OF THE INVENTION

The present invention provides recombinant PKS genes and plasmids comprising those genes, host cells comprising those genes and/or plasmids, and methods for producing polyketides with those genes, plasmids, and host cells. In one embodiment, the present invention provides a recombinant PKS gene that differs from a naturally occurring PKS gene by the replacement of one or more regions of homology in said naturally occurring gene with a non-homologous DNA sequence that encodes the same or substantially similar amino acid sequence. In one embodiment, the invention provides a plasmid comprising a recombinant PKS gene of the invention. In one embodiment, the PKS is a megalomicin synthase. In one embodiment, the host cell is an Actinomycetes, E. coli, or yeast host cell. In another embodiment, the host cell is a Streptomyces host cell. In one embodiment, the Streptomyces host cells are S. coelicolor, S. lividans, or S. venezuelae host cells.

In a preferred embodiment, the invention provides an altered PKS gene, wherein the alteration, relative to the native or naturally occurring PKS gene, removes one or more areas of sequence homology. In one embodiment, the alteration preserves the amino acid sequence of the naturally occurring PKS.

In one embodiment, the invention provides altered megalomicin synthase genes megAI and megAIII. In the naturally occurring meg genes, there are regions of sequence identity or homology between the coding sequence for the ketosynthase domain of extender module 2 (KS2) in megAI and the coding sequence for the KS domain of extender module 6 (KS6) in megAIII as well as the coding sequence for the acyltransferase (AT) domain of extender module 2 (AT2) in megAI and the coding sequence for the AT domain of extender module 6 (AT6) in megAIII. In the recombinant megAI and megAIII genes of the invention, the nucleotide sequence of one or more of the coding sequences for KS2, KS6, AT2, and AT6 has been altered to remove or reduce sequence homology, either without alteration of the encoded amino acid sequence or with alteration that preserves the function of the domain. The present invention also provides plasmids and host comprising these genes and the products of those genes.

In one embodiment, the PKS gene of the invention comprises, relative to the naturally occurring gene, additional alterations. Such alterations include but are not limited to alterations that inactivate a domain or module and alterations that substitute a domain or module with another domain or module that has a different function. For example, beta-keto modifying domains can be inactivated or added to a PKS by alteration of the PKS gene, and the specificity of an AT domain can be changed by alteration of a PKS gene. In one embodiment, the alteration is the inactivation of the KS1 domain, which may be accomplished by a point mutation, such that the PKS can be provided a synthetic diketide that is converted to a polyketide by the remaining active extender modules in the PKS, as described in U.S. Pat. Nos. 6,080,055 and 6,066,721 and PCT publication No. 99/03986, each of which is incorporated herein by reference.

In one embodiment, the invention provides a method for producing a polyketide, which method comprises replacing, in a host cell comprising PKS genes, one or more regions of sequence homology or identity within said PKS genes, with non-homologous or non-identical sequences so as to prevent or diminish recombination between such regions, and culturing said host cell under conditions such that said PKS genes are expressed and said polyketide is produced.

These and other embodiments, modes, and aspects of the invention are described in more detail in the following description, the non-limiting examples, and claims set forth below.

BRIEF DESCRIPTION OF THE DRAWINGS

FIGS. 1A and 1B are a schematic of the megalomicin polyketide synthase (meg DEBS) and corresponding meg genes. FIG. 1A shows the meg DEBS encoded by three genes of ~10 kb size. The regions of identical sequence between KS2/AT2 and KS6/AT6 are depicted below the genes by the shaded boxes. FIG. 1B shows the arrangement of modules and active sites of meg DEBS, which are identical to the erythromycin PKS (ery DEBS). The meg PKS produces 6-dEB from propionyl-CoA and 6 methylmalonyl-COA units. A KS1° mutation permits the incorporation of synthetic diketide intermediates to produce 6-dEB analogs. The abbreviations used in the FIG. are: ACP acyl carrier protein, AT acyl transferase, KS-ketosynthase, DH-dehydratase, ER-enoylreductase, KR-ketoreductase, SNPC-N-propionyl-csyteamine thioester, TE thioesterase.

The top alignment of FIG. 2 shows a sequence alignment of the identical DNA sequences in the meg coding sequence for the KS domains of modules 2 and 6 (megKS2/KS6) (SEQ ID NO: 3) with the altered sequence for module 6 (megKS6*) (SEQ ID NO: 4). Restriction sites used in assembly of the synthetic fragments are shown.

The bottom alignment of FIG. 2 shows a sequence alignment of the identical DNA sequences in the meg coding sequence for the AT domains of modules 2 and 6 (megAT2/AT6) (SEQ ID NO: 5) with the altered sequence for module 6 (megAT6*) (SEQ ID NO: 6). Restriction sites used in assembly of the synthetic fragments are shown.

Figure 3:
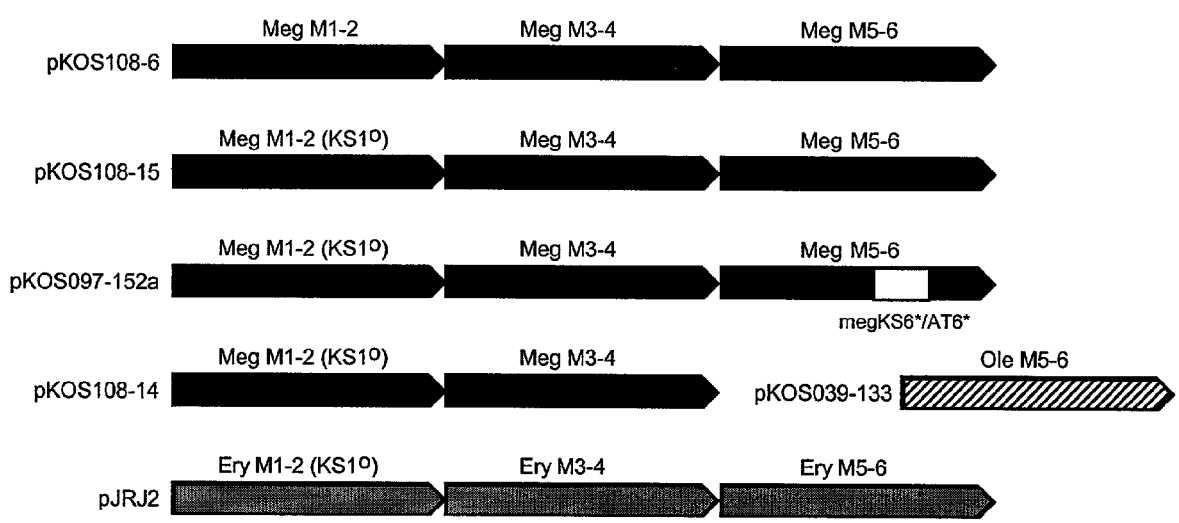

FIG. 3 shows PKS genes on various plasmids described herein.

Figure 4:
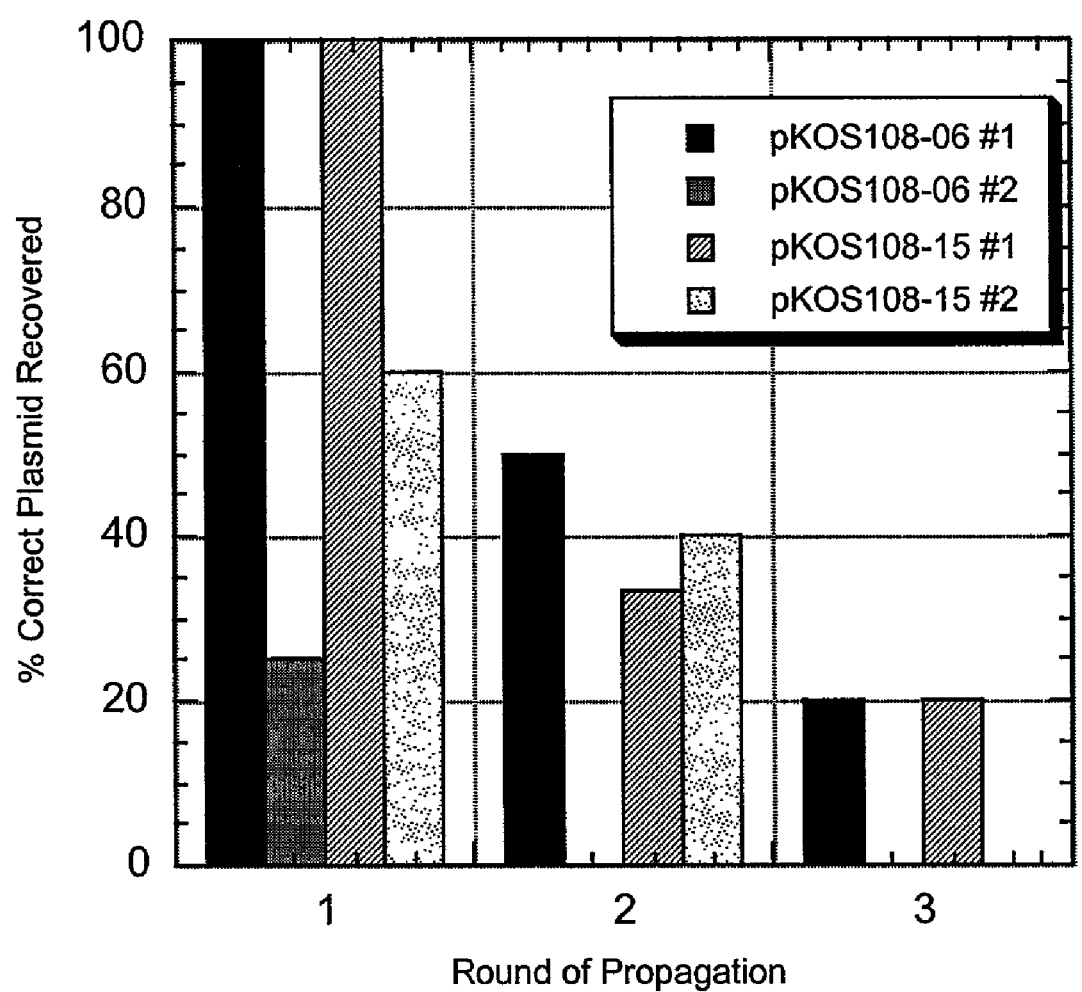

FIG. 4 shows the results of an analysis of the stability of various PKS expression plasmids through several rounds of propagation.

DETAILED DESCRIPTION OF THE INVENTION

The present invention arose out of studies with naturally occurring meg genes cloned onto plasmids for heterologous expression. In these studies, various unexpected problems were encountered, and the present invention provides solutions to those problems useful not only in the production of polyketides using the meg PKS genes but also to many other PKS genes.

Many naturally occurring PKS genes contain "regions of sequence homology" or "regions of sequence identity." As used herein, these phrases refer to two different segments in a PKS gene or gene cluster that have an identical or nearly identical nucleotide sequence. As used herein, "nearly identical" refers to two different nucleotide sequence segments that are, over the entire sequence of the segment, at least 95% identical, typically more than 98% identical, and often more than 99% identical. Each of the two segments in each homology region is at least 50 nucleotides in length, often more than 100 nucleotides in length, more often more than 250 nucleotides in length, and most often at least 500 nucleotides in length.

These segments are separated by a sequence of DNA that is usually at least 500 nucleotides in length, more often at least 1 kb in length, and usually at 2, 5, 10, 20, 30, to 50 kb in length or larger, depending ultimately on the size of the PKS gene cluster. Those of skill in the art will recognize that a PKS gene cluster for a modular PKS typically comprises at least three different open reading frames or genes. A region of homology can be composed of two segments from the same open reading frame or gene, but more often, each segment of homology will be located on a different gene from the other in the PKS gene cluster. A PKS gene cluster may have only a single region of homology or may contain 2, 3, 4, or more such regions.

The present invention teaches the benefits of removing such regions of homology by substituting one or both segments of one or more regions of homology in a PKS gene cluster with a nucleotide sequence that encodes the same amino acid sequence as the sequence substituted or with a nucleotide sequence that encodes a functionally equivalent or "substantially similar" amino acid sequence so as to destroy the region of homology in which such substitution was made. Thus, the present invention provides methods for making such genes, the genes and gene clusters made, plasmids and host cells comprising such genes, and methods for making the PKS encoded by such genes as well as the polyketides produced by such PKS. The invention is illustrated by application to the meg gene cluster.

Two meg DEBS expression plasmids were used to transform S. coelicolor CH999. See McDaniel, R., et al. 1993, and U.S. Pat. No. 5,672,491. Plasmid pKOS108-6 (see FIG. 3) encodes the wild-type meg DEBS, and pKOS108-15 (FIG. 3) encodes the same meg DEBS with a point mutation (KS1°) in the ketosynthase domain of module 1, as previously described for ery DEBS (see Jacobsen, et al., 1997 and Kao, et al., 1996 and U.S. Pat. No. 6,080,555). Efficient transformation of S. coelicolor requires the use of unmethylated DNA that is typically prepared from methylation-deficient E. coli strains such as ET12567 (dam13::Tn9, dcm6) (see MacNeil, et al., 1992). However, plasmids pKOS108-6 and pKOS108-15 could not be passaged through ET12567 without rearrangement, presumably due to intra-plasmid recombination. Therefore, these plasmids were first passaged through S. lividans JT46 (rec46), a strain deficient in intra-plasmid recombination (see Tsai, et al., 1987), to generate DNA suitable for introduction into S. coelicolor.

An analysis of plasmid stability was performed as described in Example 1B, and the results are shown in FIG. 4. The results showed that by the end of the third round of propagation, an average of only 10% of the rescued plasmids appeared to be the same as the starting expression plasmid, pKOS108-6 or pKOS108-15. Of the remaining plasmids observed, >90% contained restriction fragments that were consistent with a large deletion in the meg PKS genes. These data suggested that, in S. coelicolor, these plasmids undergo recombination between at a significant frequency. The fact that similar results were obtained for plasmid pKOS108-15, which does not produce a metabolite under the test conditions (the KS1° mutation renders the PKS inactive in the absence of added diketide), as with plasmid pKOS108-6, eliminated production of the PKS metabolite (6-dEB) as a contributing factor to the observed instability.

An analysis of the sequence of the meg genes showed significant regions of homology in the coding sequences for extender modules 2 and 6, particularly in the coding sequences for the KS and AT domains if those modules. Thus, one region of homology had segments from the coding sequence of AT2 and AT6, and another had segments from the coding sequence for KS2 and KS6. In accordance with the methods of the inventions, the megAI and megAIII genes were altered to remove these regions of homology.

Thus, the coding sequences for the KS and AT regions of module 6 that are identical to module 2 were substituted with synthetic DNA fragments to provide altered coding sequences (termed megKS6*(SEQ ID NO: 4) and megAT6* (SEQ ID NO: 6)) shown in FIG. 2. These illustrative altered coding sequences maintain the same amino acid sequence of the naturally occurring or native meg DEBS protein, but reduce the DNA sequence identity from 100% to 70%, with the longest contiguous segment of identity being 121 bp. The expression plasmid pKOS97-152a (see FIG. 3) is thus identical to pKOS108-15 with two exceptions: it contains the altered sequences shown in FIG. 2 instead of the corresponding sequences from the naturally occurring genes; and ~0.4 kb of DNA downstream of megAIII in pKOS108-15 is replaced with a λ cos site, used to facilitate plasmid construction.

Unlike the case with plasmid pKOS108-15, unmethylated plasmid pKOS097-152a DNA could be generated without rearrangement in E. coli ET12567. Plasmid pKOS097-152a was transformed into S. coelicolor CH999, and the S. coelicolor CH999/pKOS097-152a transformants were propagated and checked for plasmid stability in a manner similar to the procedure in Example 1B, below. Based on restriction enzyme analysis and comparison to authentic starting plasmid, there appeared to be no rearrangement of pKOS097-152a after four rounds of propagation in S. coelicolor CH999. Thus, the altered coding sequences prevented intra-plasmid recombination. Moreover, polyketide titers from this strain were reproducibly measured, as described in the examples below.

Thus, the present invention provides methods for constructing improved recombinant PKS genes by substitution of one or more segments of one or more homologous regions with segments that reduce or eliminate the homologous regions. In one embodiment, illustrated above, the replacement segments reduce the homology between segments in a homologous region from 100% to 70%, eliminating the homologous region. In other embodiments, the homology can be reduced to 90%, 85%, 80%, 75%, 65%, 50%, or less. Moreover, one can practice the method by altering only a portion of a segment, a segment in its entirety but no non-segment coding sequence, portions or all of both segments in a homology region but no non-segment coding sequence, and a portion or all of one or both segments together with non-segment coding regions.

The latter embodiment is illustrated herein by a replacement of one of the meg DEBS genes with a gene from another PKS gene cluster. Protein subunits from related PKS families have been used to form heterologous PKS complexes with full complemention of enzymatic activities. See PCT publication 99/61599 and U.S. Pat. No. 6,117,659, both of which are incorporated herein by reference. Specifically, the third subunit of the ery DEBS comprising extender modules 5 and 6 was co-expressed with the first two subunits of the picromycin PKS (PikAI and PikAII encoding modules 1 through 4 of the picromycin PKS) to generate hybrid 14-membered macrolactones. See Tang L., et al., 2000. Analogous hybrid PKS were made using the oleandolide PKS (ole PKS) genes (see U.S. Pat. No. 6,251,636, incorporated herein by reference). Co-expression of heterologous PKS subunits can be used in accordance with the methods of the present invention to achieve the benefits thereof, provided one selects the genes encoding such subunits as taught herein to eliminate regions of homology.

This aspect of the present invention is illustrated by a hybrid PKS in which the ole PKS OleAIII subunit was used to replace meg DEBS3 (ery DEBS3 has greater homology to meg DEBS3 than does OleAIII at the amino acid sequence level and could also be used). Integrating plasmid pKOS039-133, an OleAIII expression plasmid, was transformed into S. coelicolor CH999/pKOS108-14 (a plasmid identical to pKOS108-15 except that it lacks the megAIII gene), and plasmid stability analyzed. Because pKOS039-133 is a chromosomal integrating vector, analysis of plasmid stability was analyzed for pKOS108-14 only. After 4 rounds of propagation, there was no evidence of plasmid rearrangement, and reproducible polyketide titers were produced, as described in the Examples below.

The present invention can be applied to any PKS gene that contains a region of homology, not just naturally occurring PKS genes. To illustrate this aspect of the invention, the methods of the invention were applied to PKS genes containing mutations in KS1. Several analogs of 6-dEB have been generated by precursor directed biosynthesis, a process in which chemically synthesized N-acyl cysteamine thioester diketides are fed to S. coelicolor CH999 expressing a PKS, such as ery DEBS, in which the ketosynthase of the first extender module has been rendered inactive. This inactivation can be readily accomplished by a cys-to-ala mutation in the active site (the KS1-null or KS1° mutation; see Jacobsen et al., 1997, reviewed in McDaniel et al., 2001; see also U.S. Pat. No. 6,080,055 and the patents and patent publications cited supra). Prior to application of the methods of the present invention, it was not feasible to examine the relative efficiencies of diketide processing between meg DEBS and ery DEBS due to plasmid instability of meg DEBS plasmids. Strains made in accordance with the present invention that expressed the meg PKS having the same KS1 mutation as ery DEBS-KS1° and under the same regulatory elements (McDaniel et al., 1993), afford an opportunity to evaluate diketide precursor incorporation by meg DEBS relative to ery DEBS.

Shake flask fermentations were conducted with the engineered meg DEBS and meg/ole hybrid in the presence of racemic diketide-SNPC substrate (diketide 1, FIG. 1, and its 2,3 enantiomer). Results are summarized in the examples, below. Both strains of the invention produced 15-methyl-6dEB with the meg/ole hybrid PKS consistently yielding the highest titers. The higher titer observed with the hybrid PKS complex compared to the meg DEBS complex could result from different relative expression levels of the engineered megAIII and oleAIII genes and/or differences in kinetics of OleAIII versus MegAIII. However, the titers of both strains are comparable to those of ery DEBS-KS1° in the same host and under the same conditions and indicate that the diketide incorporation efficiency of meg DEBS is similar to that of ery DEBS.

The stability and high titer of the S. coelicolor CH999/pKOS108-14, pKOS039-133 strain facilitates production in large scale fermentation. Peak titers of 15-methyl-6dEB in 5 L fermentations conducted with glucose feeding and maintenance of diketide concentration were similar to those obtained in the small scale production with shake flask experiments above. These results indicate that expression of the PKS is reproducible, and the plasmids are stable.

Thus, the present invention provides methods for engineering PKSs to prevent homologous recombination events detrimental to PKS expression and polyketide production.

A detailed description of the invention having been provided, the following examples are given for the purpose of illustrating the invention and shall not be construed as being a limitation on the scope of the invention or claims.

EXAMPLE 1

Manipulation of DNA and Organisms (A) Strains.

Construction of plasmids was performed in E. coli XL1-Blue (Stratagene). Standard procedures were used for growth of and plasmid maintenance in E. coli (Sambrook et al., 1989) and Streptomyces organisms. Protoplast transformation procedures were used to introduce DNA into Streptomyces strains. Transformants were selected using 1 mg thiostrepton and/or 2 mg apramycin overlay (2 ml) on R2YE regeneration plates.

(B) Analysis of Plasmid Stability in Streptomyces Coelicolor.

Individual colonies from primary transformants were used to inoculate 5–6 ml of R5 (Kieser et al., 2000) or TSB media with thiostrepton (25 µg/ml) added for selection. After 3 days growth at 30° C., 2–3% of the culture volume was used to inoculate another 5 ml culture, and the remaining cells were collected for plasmid analysis. This procedure was repeated for a total of 3–4 rounds of growth and inoculation. Because the expression plasmids used in S. coelicolor contain elements for replication and selection in E. coli, analysis of plasmid content was performed by isolating total DNA from harvested cells and transforming E. coli XL1-Blue (Stratagene), which is deficient in homologous recombination (recA1). Plasmid DNA from approximately 10–20 E. coli transformants was prepared and analyzed by restriction enzyme-gel electrophoresis with comparison to the authentic starting plasmid. The results from the analysis of plasmid stability for plasmids pKOS108-6 and pKOS108-15 performed as described above are summarized in FIG. 4.

(C) Construction of pKOS108-06 and pKOS108-15 Plasmids.

Plasmid pKOS108-06 encoding the wild-type meg DEBS was prepared as described in PCT publication No. 01/27284, incorporated herein by reference. Plasmid pKOS108-15 encodes the same meg DEBS with a point mutation (Cys729A1a) in the KS domain of module 1 (KS1°), as previously described for ery DEBS (see Kao, et al., 1996). The latter plasmid was constructed as follows. A 22 kb EcoRI-BglII fragment containing the megAI and megAII genes was subcloned into pLitmus 28 (Stratagene). The 2.4 kb EcoRI-SphI fragment of this plasmid containing the KS1 domain was replaced with the same fragment in which the above mutation had been introduced by PCR mutagenesis (nt 2185–2190 of megAI changed to GCTAGC). The resulting plasmid, pKOS024-86, contains an NheI restriction site at the location of the amino acid substitution. The 22 kb EcoRI-BglII fragment from pKOS024-86 was then used to replace the corresponding fragment from pKOS108-06 to create pKOS108-15. Likewise, the 22 kb EcoRI-BglII fragment from pKOS024-86 was used to replace the corresponding fragment from pKOS024-24 to generate pKOS108-14, which contains only the megAI (KS1°) and megAII genes.

EXAMPLE 2

Construction of Plasmids of the Invention

Three separate DNA fragments, a PstI-BamHI fragment (nt 26,739–26,947), a BamHI-BsmI fragment (nt 26,947–27,267), and an SfaNI-FseI fragment (nt 27,697–27,987) spanning the KS6 and AT6 regions of the megAIII gene were synthesized (Retrogen) and cloned into pCR-Blunt II-TOPO (Invitrogen). Each of the DNA segments alters the natural codons to those shown in FIG. 2. The cloned synthetic fragments were verified by DNA sequencing and used to construct pKOS097-152a as follows.

First, a cassette containing the phage λ cos site was introduced downstream of the megAIII gene. A 350 bp segment at the end of the megAIII gene was PCR amplified using the two oligonuceotide primers 5'-d(TTTGACGTG-TACCCACCCGGTCACCAGGAG) (SEQ ID NO: 1) and 5'-d(TTTGAATTCTCTAGATCATGCCCTCTC-CCCGCTCAACAACCAGGC) (SEQ ID NO: 2) and cloned into pCRBlunt II (Invitrogen) to create pKOS097-87B. The 9.2 kb BglII-XbaI fragment containing most of megAIII from pKOS108-06 was subcloned into pLitmus28 (New England BioLabs) to generate pKOS097-81. The 4.3 kb PstI-XbaI fragment from pKOS097-81 was then subcloned into pLitmus 28 to make pKOS097-84. The 0.35 kb AflIII-EcoRI fragment from pKOS097-87B and the 4.0 kb AflIII-PstI fragment from pKOS097-84 were ligated together with PstI-EcoRI digested pLitmus38 (New England BioLabs), resulting in pKOS097-90. This was followed by the insertion of the 4.9 kb SpeI-PstI fragment from pKOS097-81 into the corresponding sites of pKOS097-90 to generate pKOS097-90A. The 9.2 kb BglII-EcoRI fragment of pKOS097-92a was combined with the megAI and megAII genes in pHU152', a cloning vector containing the desired cos site. This plasmid was named pKOS097-92 and contains the megAI-AIII genes with a cos site downstream of megAIII flanked by an XbaI site.

Next, the PstI-BsmI fragment in pKOS097-90 was replaced with the two PstI-BamHI and BamI-BsmI synthesized DNA fragments from above. The PstI-SfaNI fragment from pKOS097-90 and the synthesized FseI-SfaNI fragment were joined together to replace the PstI-FseI fragment of pKOS097-90 to make pKOS097-152. Finally, pKOS097-152a was constructed by a four fragment ligation using the 4.9 kb BglII-PstI fragment from pKOS098-81, the 2.6 kb PstI-BlpI fragment from pKOS097-152, the 2.0 kb BlpI-XbaI fragment from pKOS097-92, and with pKOS108-14 digested with BglII-XbaI. The ligation mixture was packaged in vitro using a Gigapack-III Gold (Stratagene) kit.

EXAMPLE 3

Fermentation and Analysis of Polyketide Titers

Fermentation studies were initiated from frozen cell bank vials. Primary seed cultures were established by inoculating 50 ml of FKA medium with a cell bank vial and cultivating for 3 days. For shake flask studies, replicate flasks containing 35 ml of production medium were inoculated with 1.75 ml (5% v/v) of the primary seed culture. For the production of 15-methyl-6-dEB, 40% racemic (2S, 3R and 2R, 3S) 2-methyl-3-hydroxy-hexanoic acid, N-propionyl-cysteamine thioester (SNPC) in DMSO was fed (2 g/L final) 2 days after inoculation and maintained above 1 g/L. Flasks were incubated for 6-10 days with 1 ml samples withdrawn as necessary and stored at −20° C. until analysis. All media were supplemented with 10 ml of 50% (v/v) Antifoam B (J. T. Baker, Phillipsburg, N.J.) per liter of culture volume as post-sterile additions. Seed cultures were also supplemented with 50 mg/L thiostrepton (Calbiochem, La Jolla, Calif.).

Bioreactor studies were performed in B. Braun MD 5 L fermentors with 3 L of FKA medium without HEPES operated at 30° C., pH 6.5, 0.3 VVM airflow, and 600 rpm agitation. Dissolved oxygen concentration and pH were monitored using autoclaveable electrodes (Mettler Toledo, Wilmington, Mass.). Under these operating conditions, dissolved oxygen was maintained above 50% by automatic increase of agitation as necessary. Foaming was controlled by automatic addition of 50% (v/v) Antifoam B solution. The pH was controlled by automatic addition of 2.5 N sodium hydroxide or sulfuric acid. Bioreactors were inoculated with 5% (v/v) secondary seed culture prepared by sub-culturing 25 ml of primary seed into 500 ml of FKA and cultivation for 2 days. Samples were withdrawn as necessary and stored at −20° C. for later analysis.

Quantitation of diketide-SNPC and 15-methyl-6-dEB was performed using a Hewlett-Packard 1090 HPLC equipped with a diode array detector and an Alltech 500 evaporative light scattering detector as described previously (Leaf, et al., 2000). Measurement uncertainty was typically 10% by this procedure.

S. coelicolor CH999/pKOS097-152a fermented as described above in the presence of the propyl diketide substrate produced a titer of ~22 mg/L of 15-methyl-6-dEB. Under these conditions, the ery DEBS-KS1° strain (harboring plasmid pJRJ2) produces 30 mg/L of 15-methyl-6-dEB. S. coelicolor CH999/pKOS108-14, pKOS039-133 fermented as described above in the presence of the propyl diketide substrate produced a titer of 43 mg/L of 15-methyl-6dEB.

Although the present invention has been described in detail with reference to one or more specific embodiments, those of skill in the art will recognize that modifications and improvements are within the scope and spirit of the invention, as set forth in the claims which follow. All publications and patent documents cited herein are incorporated herein by reference as if each such publication or document was specifically and individually indicated to be incorporated herein by reference. Citation of publications and patent documents is not intended as an admission that any pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A recombinant modified polyketide synthase (PKS) gene obtained by modifying a PKS gene comprising a first region and second region,
wherein said first region of said PKS gene has at least 95% sequence identity to said second region;
wherein in said modified PKS gene said second region is replaced with a nucleotide sequence that has less sequence identity to the first region than in the unmodified gene, but encodes the same amino acid sequence as in the unmodified gene; and
whereby recombination between plasmids comprising the modified gene is prevented.

2. A plasmid that comprises the modified PKS gene of claim 1.

3. A culture of Actinomycete, *E. coli* or yeast cells that comprise the modified PKS gene of claim 1.

4. The Actinomycete cells of claim 3 are *Streptomyces*.

5. The cells of claim 4, wherein said unmodified PKS gene is megAIII.

6. A modified recombinant polyketide synthase (PKS) gene made by a method comprising the following steps:
a) identifying a first segment of said PKS gene having at least 95% sequence identity to a second segment of said PKS gene; and
b) replacing said second segment with a nucleotide sequence that has less sequence identity to said first segment, but encodes the same amino acid sequence as in the gene without said replacement;
whereby recombination between plasmids comprising the modified gene is prevented.

7. The recombinant PKS gene of claim 6, wherein said first segment of said PKS gene has at least 98% sequence identity to said second segment of said PKS gene.

8. The recombinant PKS gene of claim 6, wherein said first segment of said PKS gene has at least 99% sequence identity to said second segment of said PKS gene.

9. The recombinant PKS gene of claim 6, wherein each of the two segments is at least 50 nucleotides in length.

10. The recombinant PKS gene of claim 6, wherein each of the two segments is at least 100 nucleotides in length.

11. The recombinant PKS gene of claim 6, wherein each of the two segments is at least 250 nucleotides in length.

12. The recombinant PKS gene of claim 6, wherein each of the two segments is at least 500 nucleotides in length.

13. A method for increasing the production of a polyketide or a polyketide synthase (PKS) protein in a cell, comprising the steps of:
   a) providing a recombinant PKS gene made by a method comprising the following steps:
      i) identifying a first segment of said PKS gene having at least 95% sequence identity to a second segment of said PKS gene; and
      ii) replacing said second segment with a nucleotide sequence that has less sequence identity to said first segment, but encodes the same amino acid sequence as in the gene without said replacement; and
   b) expressing the recombinant PKS gene made by the step of a) in the cell.

* * * * *

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: oligonucleotide primer

```
<400> SEQUENCE: 1
tttgacgtgt acccacccgg tcaccaggag                                    30

<210> SEQ ID NO 2
<211> LENGTH: 45
<212> TYPE: DNA
<213> ORGANISM: Artificial Sequence
<220> FEATURE:
<223> OTHER INFORMATION: oligonucleotide primer

<400> SEQUENCE: 2
tttgaattct ctagatcatg ccctctcccc gctcaacaac caggc                   45

<210> SEQ ID NO 3
<211> LENGTH: 615
<212> TYPE: DNA
<213> ORGANISM: Artificial Sequence
<220> FEATURE:
<223> OTHER INFORMATION: megKS2

<400> SEQUENCE: 3
tgcagcggtt gtcggtggcg gtgcgggagg ggcgtcgggt gttgggtgtg gtggtgggtt   60
cggcggtgaa tcaggatggg gcgagtaatg ggttggcggc gccgtcgggg gtggcgcagc  120
agcgggtgat tcgcgggcg tggggtcgtg cgggtgtgtc gggtggggat gtgggtgtgg  180
tggaggcgca tgggacgggg acgcggttgg gggatccggt ggagttgggg gcgttgttgg  240
ggacgtatgg ggtgggtcgg ggtgggtgg gtccggtggt ggtgggttcg gtgaaggcga  300
atgtgggtca tgtgcaggcg gcggcgggtg tggtgggtgt gatcaaggtg gtgttggggt  360
tgggtcgggg gttggtgggt ccgatggtgt gtcggggtgg gttgtcgggg ttggtggatt  420
ggtcgtcggg tgggttggtg gtggcggatg gggtgcgggg gtggccggtg ggtgtggatg  480
gggtgcgtcg gggtggggtg tcggcgtttg gggtgtcggg gacgaatgct catgtggtgg  540
tggcggaggc gccggggtcg gtggtggggg cggaacggcc ggtggagggg tcgtcgcggg  600
ggttggtggg ggtgg                                                  615

<210> SEQ ID NO 4
<211> LENGTH: 615
<212> TYPE: DNA
<213> ORGANISM: Artificial Sequence
<220> FEATURE:
<223> OTHER INFORMATION: megKS6

<400> SEQUENCE: 4
tgcagcgcct ctccgtcgcc gtccgcgagg gccgccgagt cctcggcgtc gtcgtcggct   60
cggccgtcaa ccaagacggc gcgtcaaacg gcctcgccgc gccctccggc gtcgcccagc  120
agcgcgtcat acgccgcgcg tggggacgcg ccggagtatc gggcggcgac gtcggagtcg  180
tcgaggccca cggcaccggc acccgcctcg ggatcccgt cgagctgggc gccctcctgg  240
gcacgtacgg cgtcggccgc ggcggcgtcg gcccggtcgt cgtcggcagc gtcaaggcca  300
acgtcggcca cgtccaggcc gcggccgcg tcgtcgggt catcaaggtc gtcctcggcc  360
tcggccgcgg gctggtcggc ccgatggtct gccgcggcgg cctcagcggc ctcgtcgact  420
ggtcgtccgg cggcctggtc gtcgcggacg gggtccgcgg ctggccggtc ggcgtcgacg  480
gcgtccgccg gggcggcgtc tcggcgttcg gcgtcagcgg gacgaatgct catgtggtgg  540
tggcggaggc gccggggtcg gtggtggggg cggaacggcc ggtggagggg tcgtcgcggg  600
ggttggtggg ggtgg                                                  615
```

```
<210> SEQ ID NO 5
<211> LENGTH: 426
<212> TYPE: DNA
<213> ORGANISM: Artificial Sequence
<220> FEATURE:
<223> OTHER INFORMATION: megAT2

<400> SEQUENCE: 5
ccggtgtggt gtcggggtg gcgtcgggtg gtggtgtggt gtttgttttt cctggtcagg      60
gtggtcagtg ggtggggatg gcgcgggggt tgttgtcggt tccggtgttt gtggagtcgg     120
tggtggagtg tgatgcggtg gtgtcgtcgg tggtgggtt ttcggtgttg ggggtgttgg      180
agggtcggtc gggtgcgccg tcgttggatc gggtggatgt ggtgcagccg gtgttgttcg     240
tggtgatggt gtcgttggcg cggttgtggc ggtggtgtgg ggttgtgcct gcggcggtgg     300
tgggtcattc gcagggggag atcgcggcgg cggtggtggc gggggtgttg tcggtgggtg     360
atggtgcgcg ggtggtggcg ttgcgggcgc gggcgttgcg ggcgttggcc ggccacggcg     420
gcatgg                                                               426

<210> SEQ ID NO 6
<211> LENGTH: 426
<212> TYPE: DNA
<213> ORGANISM: Artificial Sequence
<220> FEATURE:
<223> OTHER INFORMATION: megAT6

<400> SEQUENCE: 6
ccggtgtggt gtcggggtg gcgtcgggtg gtggtgtggt gtttgttttt cctggtcagg      60
gtggtcagtg ggtggggatg gcgcgggggt tgttgtcggt tccggtgttt gtggagtcgg    120
tcgtggagtc cgatgcggtc gtgtcgagcg tcgtcggctt cagcgtgctg ggcgtcctgg    180
agggccgcag cggcgccccg agcctggacc gcgtcgacgt ggtccagccg gtcctgttcg    240
tggtcatggt cagcctggcc cgcctgtggc gctggtgcgg cgtggtcccg gccgccgtgg    300
tcggccacag ccaggcgag atcgccgccg cggtcgtggc cggcgtcctg agcgtcggcg    360
acggcgcccg cgtcgtggcc ctgcgcgccc gcgccctgcg cgccctggcc ggccacggcg    420
gcatgg                                                              426
```